(12) United States Patent
Saeki

(10) Patent No.: US 7,982,779 B2
(45) Date of Patent: Jul. 19, 2011

(54) IMAGE PROCESSING DEVICE AND IMAGE PROCESSING METHOD

(75) Inventor: Yasushi Saeki, Osaka (JP)

(73) Assignee: Keyence Corporation, Osaka (JP)

( * ) Notice: Subject to any disclaimer, the term of this patent is extended or adjusted under 35 U.S.C. 154(b) by 787 days.

(21) Appl. No.: 11/055,270

(22) Filed: Feb. 10, 2005

(65) Prior Publication Data

US 2005/0178949 A1 Aug. 18, 2005

(30) Foreign Application Priority Data

Feb. 12, 2004 (JP) ................. 2004-034514

(51) Int. Cl.
*H04N 5/225* (2006.01)
*H04N 7/18* (2006.01)
*G06K 9/00* (2006.01)

(52) U.S. Cl. ........... 348/218.1; 348/86; 348/92; 348/94; 382/141; 382/144; 382/145

(58) Field of Classification Search ............ 348/211.12, 348/218.1, 207.99–207.2, 86–92; 382/141–152
See application file for complete search history.

(56) References Cited

U.S. PATENT DOCUMENTS

| | | | |
|---|---|---|---|
| 5,262,871 A * | 11/1993 | Wilder et al. ................. | 348/307 |
| 6,047,042 A | 4/2000 | Khutoryansky et al. | |
| 6,137,531 A | 10/2000 | Kanzaki et al. | |
| 6,535,630 B1 | 3/2003 | Saeki ........................ | 382/162 |
| 6,670,991 B1 * | 12/2003 | Takagi et al. ................ | 348/349 |
| 6,920,241 B1 * | 7/2005 | Dutta-Choudhury et al. ........................ | 382/141 |
| 6,970,588 B1 * | 11/2005 | Komatsu ..................... | 382/141 |
| 6,987,874 B2 * | 1/2006 | Hirose et al. ................. | 382/145 |
| 7,161,619 B1 * | 1/2007 | Niida et al. .............. | 348/207.11 |
| 7,231,079 B2 * | 6/2007 | Okuda et al. ................. | 382/145 |
| 2002/0113234 A1 * | 8/2002 | Okuda et al. .................... | 257/48 |
| 2003/0185432 A1 * | 10/2003 | Hong et al. ................... | 382/151 |
| 2004/0061712 A1 | 4/2004 | Sogawa | |
| 2004/0105595 A1 | 6/2004 | Watanabe et al. | |

(Continued)

FOREIGN PATENT DOCUMENTS

EP 0 837 323 A2 4/1998

(Continued)

OTHER PUBLICATIONS

European Search Report for corresponding European Application No. EP 05 00 3046.9 dated Jul. 28, 2005.

(Continued)

*Primary Examiner* — Sinh Tran
*Assistant Examiner* — Christopher K Peterson
(74) *Attorney, Agent, or Firm* — Kilyk & Bowersox, P.L.L.C.

(57) ABSTRACT

In an inspection of a substance in which a first region is made of black resin and a second region is made of a metal, a portion surrounding the first region is registered as a first imaging range, and a portion surrounding the second region is registered as a second imaging range. As an imaging condition for the first region, a relatively slow shutter speed is registered such that an image does not become dark. Further, as an imaging condition for the second region, a relatively fast shutter speed is registered such that an image does not have unduly high white levels. As such, the imaging range and condition set by a user are supplied to a CCD camera, and then image processing is performed on a captured image from the CCD camera by an image processing device main body.

16 Claims, 8 Drawing Sheets

U.S. PATENT DOCUMENTS

2005/0117017 A1 * 6/2005 Baer .................... 348/87

FOREIGN PATENT DOCUMENTS

| | | |
|---|---|---|
| EP | 1 403 615 A2 | 3/2004 |
| JP | 60-236592 | 11/1985 |
| JP | 11-103410 | 4/1999 |
| JP | 11-122540 | 4/1999 |
| JP | 3007392 | 11/1999 |
| JP | 2000-242261 | 9/2000 |
| JP | 2000-329536 | 11/2000 |
| JP | 2003-109027 | 4/2003 |
| WO | WO 02/065396 A1 | 8/2002 |

OTHER PUBLICATIONS

Invitation pursuant to Article 94(3) and Rule 71(1) EPC (regarding consultation by telephone with the applicant) issued by the European Patent Office in corresponding European Patent Application No. 05 003 046.9 dated May 15, 2009 (5 pages).

Office Action issued in corresponding Japanese Patent Application No. 2004-034514 on Feb. 23, 2010 with English translation "Notification of Reason for Refusal" attached (15 pages).

* cited by examiner

| GROUP | IMAGING RANGE | IMAGING CONDITION |
|---|---|---|
| Gr1 | UPPER LEFT | SHUTTER 1/500, GAIN 5 |
| Gr2 | UPPER RIGHT | SHUTTER 1/2000, GAIN 6 |
| Gr3 | LOWER LEFT | SHUTTER 1/500, GAIN 5 |
| Gr4 | LOWER RIGHT | SHUTTER 1/2000, GAIN 6 |

-- Prior Art --

-- Prior Art --

IMAGE PROCESSING DEVICE AND IMAGE PROCESSING METHOD

This application claims foreign priority based on Japanese patent application JP 2004-034514, filed on Feb. 12, 2004, the contents of which is incorporated herein by reference in its entirety.

BACKGROUND OF THE INVENTION

1. Field of the Invention

The present invention relates to an image processing device and an image processing method.

2. Description of the Related Art

An image processing device is used for the inspection of various substances such as IC (Integrated Circuit) electronic components during the manufacturing process or after manufacture, for example, the inspection such as the measurement of the size of the substance, or the existence of defects or stains (for example, Japanese Patent Laid-Open No. 2000-329536).

As shown in FIG. 9, in the related art, such an image processing device 1 has a camera 2 having a solid-state image element such as a CCD (charge coupled device), an image processing device main body 3, a monitor 4 for displaying the result of the inspection or measurement by the image processing device main body 3, and cables 5 and 6 for detachably connecting the camera 2 and the image processing device main body 3, and the image processing device main body 3 and the monitor 4, respectively. In the related-art image processing device 1, an entire view field region 7 of the solid-state image element (CCD effective pixel region) or a central region other than a peripheral region of the entire view field region 7 is fixed as an imaging range 8 (FIG. 10). An image (captured image) of the imaging range 8 is transmitted from the camera 2 to the image processing device main body 3 to be processed.

As seen from the above description, in the related-art image processing device 1, the entire view field region (CCD effective pixel region) 7 of the solid-state image element of the camera 2 or the central region is fixed as the imaging range 8 and the captured image is transmitted to the image processing device main body 3. In the related art, the central region is fixed as the imaging range 8. This is generally because the memory space of the image processing device main body 3 or the display of the monitor 4 is limited. In this case, the entire view field region (CCD effective pixel region) 7 of the solid-state image element of the camera 2 cannot be effectively utilized. Even if the substance, that is, an inspection object enters the entire view field region 7, when it deviates from the imaging range 8, the inspection or measurement is needed to be performed again after relatively moving the inspection object or the camera 2.

Further, in order to increase precision of the inspection or measurement, when the image is captured with enlarged scale (with changed magnification), the substance may not enter the imaging range 8. In this case, the inspection or measurement is also needed to be performed again after relatively moving the inspection object or the camera 2.

In recent years, the camera 2 tends to adapt the solid-state image element having high pixel density such as 2 mega pixels, 4 mega pixels, or 7 mega pixels. When the camera that is used in combination with the image processing device main body 3 is replaced with the newest camera having high pixel density, the entire view field region 7 is enlarged with the replacement of the camera. In this case, however, the imaging range 8 to be actually processed is still fixed, and thus there is a problem in that the newest camera introduced is of no value.

Further, even when the image processing device main body 3 capable of utilizing the entire view field region 7 of the newest camera having high pixel density is tentatively manufactured, the image processing device main body 3 is needed to have an expanded memory space, and it takes a long time to transmit the captured image from the camera 2 to the image processing device main body 3. As a result, there is a problem in that the image cannot be processed at high speed.

SUMMARY OF THE INVENTION

Therefore, it is an object of the present invention to provide an image processing device and an image processing method that can effectively utilize an entire view field region of a solid-state image element of a camera without degrading the transmission rate of a captured image from the camera to an image processing device main body.

It is another object of the present invention to provide an image processing device and an image processing method that can effectively utilize the entire view field region of the solid-state image element of the camera without relatively moving the camera and an inspection object to increase precision of an inspection or measurement.

It is still another object of the present invention to provide an image processing device and an image processing method that can effectively utilize the entire view field region of the solid-state image element of the camera with a practically satisfactory processing rate to increase precision of the inspection or measurement even if the image processing device is provided with the camera having high pixel density.

It is a further object of the present invention to provide an image processing device and an image processing method that can effectively utilize the entire view field region of the solid-state image element of the camera to perform the inspection or measurement even if an image is captured with an enlarged scale so as to increase precision of the inspection or measurement.

In order to achieve the above-described technical objects, according to a first aspect of the present invention, there is provided an image processing device having a solid-state image element camera that captures an image of an inspection object, an image processing device main body that receives and process the captured image from the camera, and a monitor that displays an inspection or measurement result by the image processing device main body. The image processing device main body has a storing section that stores an imaging range of the solid-state image element camera set by a user, a transmitting section that reads the imaging range stored in the storing section and transmits a signal about the imaging range to the solid-state image element camera, and a receiving section that receives a captured image signal of the imaging range from the solid-state image element camera. The image processing device performs an image process based on the captured image signal received by the receiving section.

According to the image processing device according to the first aspect of the present invention, the user can arbitrarily set the imaging range, unlike the related art in which the imaging range is fixed. Thus, even if the image processing device is provided with the camera having high pixel density, the entire view field region of the solid-state image element of the camera can be effectively utilize to set the imaging range, without degrading the transmission rate of the captured image from the camera to the image processing device main body. Thus, precision of the inspection or measurement can be increased without relatively moving the camera and the inspection object. Therefore, even if the image is captured with the camera having high pixel density, the entire view field region of the solid-state image element of the camera can be effectively utilized with the practically satisfactory process rate, and thus precision of the inspection or measurement can be increased.

In the image processing device according to the present invention, the camera and the image processing device main body may be connected to each other via a cable or the camera and the image processing device main body may be incorporated. Further, the imaging range may be set with an external apparatus connected to the image processing device main body. Alternatively, the imaging range may be set with the image processing device main body. When the imaging range is set by the external apparatus, the imaging range can be set during the image process by the image processing device main body.

In order to achieve the above-described technical objects, according to a second aspect of the present invention, there is provided an image processing device having a solid-state image element camera that captures an image of an inspection object, an image processing device main body that receives a captured image from the camera and performs an image process, and a monitor that displays an inspection or measurement result by the image processing device main body. The image processing device main body is switchable between a setup mode in which an imaging range is set and an operation mode in which an image process is performed. In the setup mode, an imaging range assigned by a user is transmitted to the solid-state image element camera, the captured image transmitted from the solid-state image element camera is displayed on the monitor, and the imaging range determined by the user is stored in a storing section. Further, in the operation mode, a signal about the imaging range stored in the storing section is transmitted from the image processing device main body to the solid-state image element camera such that the imaging range of the solid-state image element camera is set, and the image processing device main body receives and processes a captured image of the imaging range in an image captured by the solid-state image element camera.

The image processing device main body has an assigning section that assigns the imaging range on behalf of the user, a transmitting section that transmits the imaging range assigned by the assigning section to the solid-state image element camera, a receiving section that receives the signal about the captured image of the assigned imaging range from the solid-state image element camera, a monitor display control section that transmits the captured image received from the camera to the monitor and causes the monitor to display the captured image of the imaging range, and a storing section that stores the imaging range determined by the user. In the setup mode, the imaging range assigned by the user is transmitted to the solid-state image element camera, the captured image transmitted from the solid-state image element camera is displayed on the monitor, and the imaging range determined by the user is stored in the storing section. Therefore, the user can set the imaging range while viewing the monitor.

DETAILED DESCRIPTION OF THE INVENTION

Hereinafter, a preferred embodiment of the present invention will be described with reference to FIGS. 1 to 8.

Figures 1, 2:
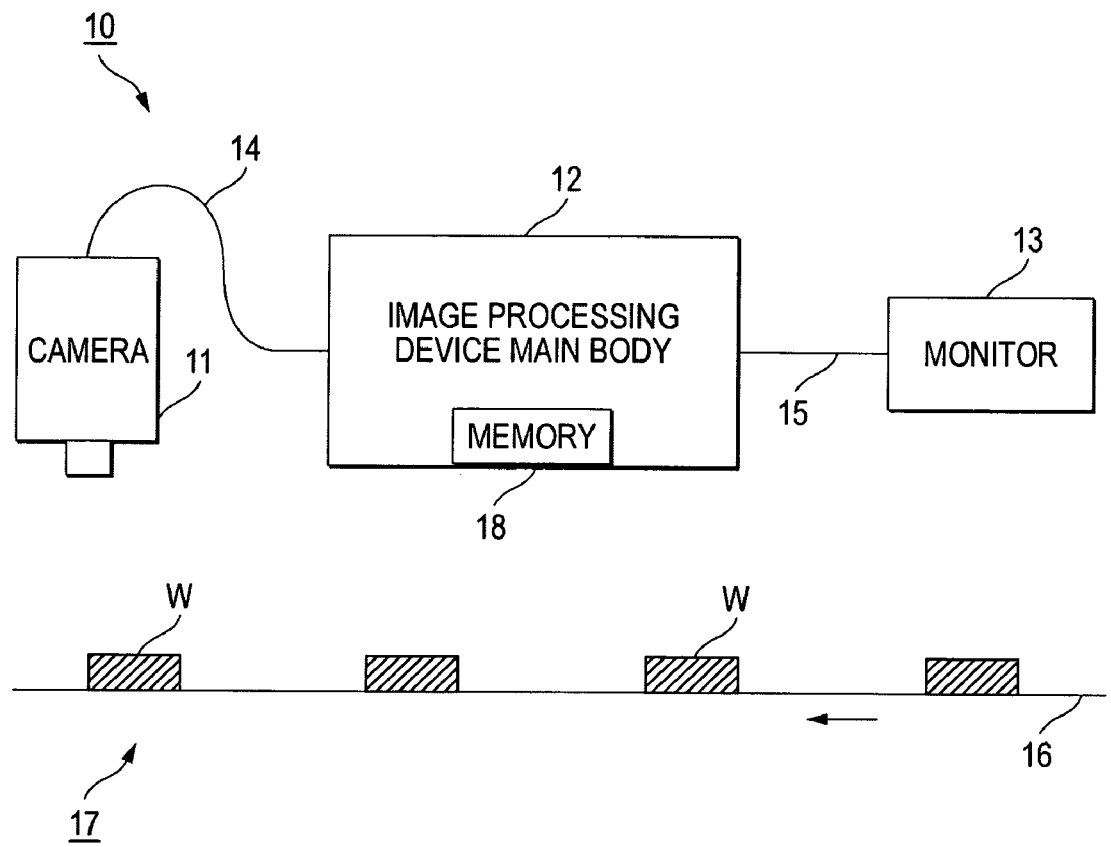
FIG. 1 is a diagram showing an entire configuration of an image processing device according to an embodiment of the present invention.
FIG. 2 is a diagram for explaining a registration example of an imaging mode that is set in advance by the image processing device according to the embodiment of the present invention.

As shown in FIG. 1, an image processing device 10 of the embodiment has general elements as described in the related art, that is, a CCD camera 11, an image processing device main body 12, a monitor 13, and cables 14 and 15 that connect them to each other. The CCD camera 11, the image processing device main body 12, and the monitor 13 are separatable from each other by removing the cables 14 and 15. The CCD camera 11 is fixedly arranged on an inspection station 17 of an inspection line 16. An inspection object (substance) W flowing on the inspection line 16 at a predetermined tact temporarily stops in a defined location on the inspection station 17. In this state, an image of the inspection object W is captured by the camera 11.

As exemplarily shown in FIG. 2, a memory 18 of the image processing device main body 12 stores an imaging mode arbitrarily set by a user, specifically, an imaging range and an imaging condition. Whenever the image of the same inspection object is captured by the camera 11, the imaging mode of the CCD camera 11 can be changed according to the imaging mode stored in the memory 18.

A setup screen of the imaging mode exemplarily shown in FIG. 2 will be described. The user can register the imaging modes of first to fourth groups Gr1 to Gr4 and can arbitrarily set the imaging range and the imaging condition of the camera for each group. The user may perform the setup work with the image processing device main body 12 or with an external apparatus connected to the image processing device main body 12, for example, a personal computer, while viewing the monitor 13. When the imaging range and the imaging condition are set by the external apparatus, the setup work may be performed during an image process by the image processing device main body 12. The imaging range and the imaging condition set in such a manner are stored in the memory 18.

When the image processing device main body 12 is provided with a section that sets the imaging range and the imaging condition, the image processing device main body 12 is preferably switchable between a setup mode that sets the imaging range and the imaging condition and an operation mode that captures an image through the camera and processes the captured image. The imaging mode registered by the user in the setup mode, that is, the imaging range and the imaging condition are stored in the memory 18. In the operation mode, the imaging mode stored in the memory 18 is read and signals about the imaging range and the imaging condition read are supplied from the image processing device main body 12 to the CCD camera 11, such that the setup of the CCD camera 11 is performed.

More specifically, in the setup mode, the user assigns the imaging range and/or imaging condition through an assigning section (not shown) of the image processing device main body 12, and the imaging range and/or imaging condition assigned by the user is transmitted to the CCD camera 11. Then, a monitor display control section (not shown) of the image processing device main body 12 transmits the captured image of the assigned imaging range and/or imaging condition received from the CCD camera 11 to the monitor 13 and causes the monitor 13 to display the captured image of the assigned imaging range and/or imaging condition. The user can determined the imaging range and/or imaging condition while viewing the monitor 13 and the imaging range and/or imaging condition determined by the user is stored in the memory 18.

Figure 4:
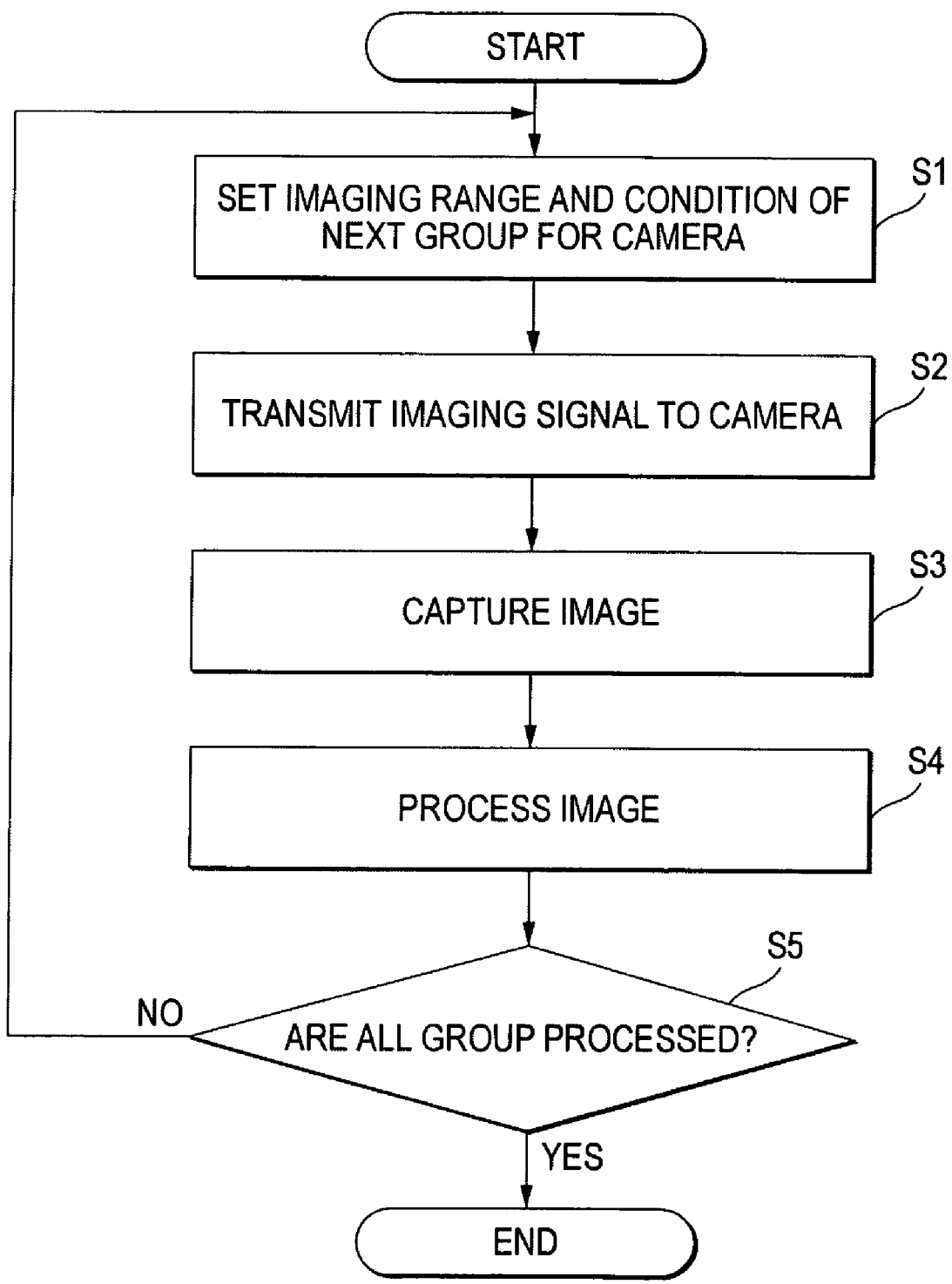
FIG. 4 is a flowchart showing an example of a procedure of a process that is performed by the image processing device according to the present invention.
Figure 5:
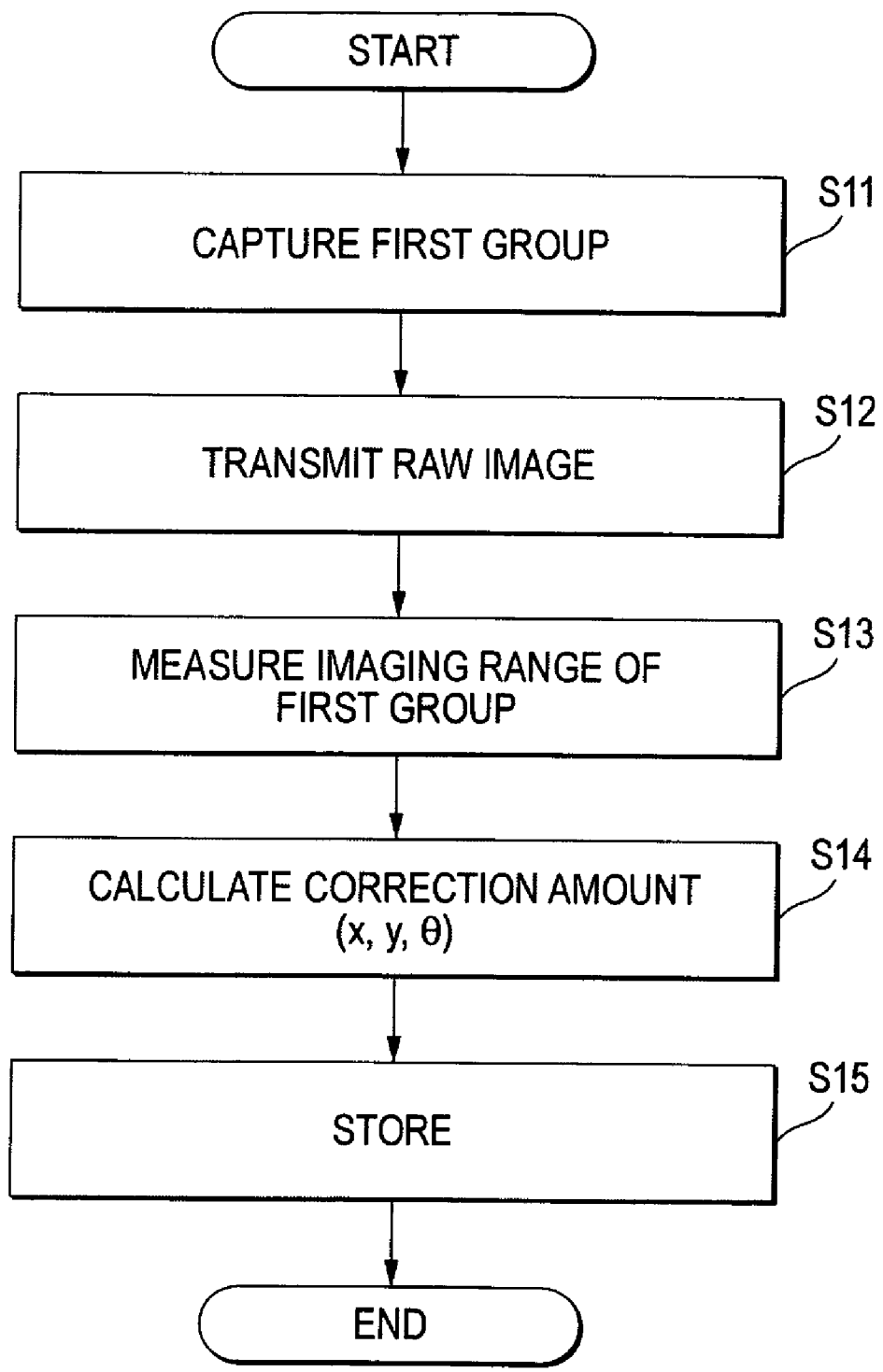
FIG. 5 is a flowchart showing an example of a position correction method as a pre-process included in the image process.

The setup of the imaging mode will be described in detail with reference with FIGS. 4 and 5. Referring to FIG. 2, the imaging range 'UPPER LEFT' in the group Gr1 means that an upper left portion with respect to a CCD effective pixel region 20 of the CCD camera 11 is registered as a first imaging range 21a. Similarly, the imaging range 'UPPER RIGHT' in the group Gr2 means that an upper right portion with respect to the CCD effective pixel region 20 is registered as a second imaging range 21b. In the setup mode, when an arbitrary portion within the CCD effective pixel region 20 is assigned as 'UPPER LEFT', 'UPPER RIGHT' or the like as described above, the range is preferably displayed on the monitor 4. Further, after confirming the range on the monitor 4, the user may allow the range to be stored in the memory 18. In such a registration method of the imaging range, preferably, the user may previously set the size of the imaging range.

Specifically, in an example of the registration shown in FIG. 2, based on the size of the imaging range 21 previously set and registered by the user, a location where the imaging range 21 is set is indicated and determined by selecting 'UPPER LEFT' or the like, such that the determined imaging range is stored in the memory 18. Further, among the imaging condition shown in FIG. 2, for example, 'SHUTTER 1/500' represents a shutter speed. 'GAIN 5' or 'GAIN 6' represents the amplification factor of a CCD output signal. In the arrangement location setup of the imaging range 21, a coordinate X(+), Y(+) with an upper left corner as an origin may be indicated and registered. Further, for example, the shutter speed of the imaging condition changes brightness (exposure time). In addition, as registerable parameters as the imaging condition, that is, as the registerable imaging conditions, zoom (magnification), scanning modes, diaphragms, illumination or the like may be included.

The number of the groups Gr1 to Gr4 is not limited, and this is just an example. The first to fourth groups Gr1 to Gr4 correspond to the number of shutter times of (trigger number) with respect to one inspection object. The first group Gr1 substantially means a first trigger, that is, a first shutter with respect to the same inspection object, the second group Gr2 substantially means a second trigger, the third group Gr3 substantially means a third trigger, and the fourth group Gr4 substantially means a fourth trigger.

An example of a procedure in which the camera 11 captures the image of the inspection object and the image processing device main body 12 receives and processes the captured image will be described with reference to a flowchart of FIG. 4.

If the inspection object W stops at a predetermined position on the inspection station 17, the image processing device main body 12 synchronously receives a process start signal that is supplied from an exterior, such that the process is started. In a step S1, the imaging range and the imaging condition registered as the first group Gr1 are read from the memory 18, and the signals about the imaging range and the imaging condition of the first group Gr1 are supplied from the image processing device main body 12 to the CCD camera 11, such that the setup of the CCD camera 11 is performed. Then, the CCD camera 11 captures an image according to the imaging condition of the first group Gr1 (step S2).

In a next step S3, in the raw image captured by the CCD camera 11 (image of the entire view field region 20), the image (captured image) of the imaging range of the first group Gr1 is transmitted from the CCD camera 11 to the image processing device main body 12. In a step S4, the image processing device main body 12 receives the image (captured image) and performs the same image process as that in the related art.

Here, the image process in the step S4 includes a position correction (x, y, θ) of an image about an x axis, a y axis, and a rotation θ, and further it means a process required for a desired inspection or measurement (for example, the size, the existence of defects, the number, the edge detection). The image process including the position correction is well-known, and thus the detailed description thereon will be omitted. As for the position correction, the procedure thereof will be described with reference to FIG. 5. After capturing the image with respect to the first group Gr1 in a step S11, the raw image is transmitted from the camera 11 to the image processing device main body 12 (step S12), and the measurement of the imaging range set on the first group is performed by the image processing device main body 12 (step S13). Then, the correction amount (x, y, θ) is calculated based on the measurement. The correction amount (x, y, θ) is stored in the memory of the image processing device main body 12. The correction amount (x, y, θ) is used for the pre-process (position correction) that is included in the image process of the second, third, or fourth group.

After the image of the first group Gr1 is captured and processed, the process returns to the step S1. Here, the imaging range and the imaging condition registered as the second group Gr2 are read from the memory 18, and the signals about the imaging range and the imaging condition of the second group Gr2 are supplied from the image processing device main body 12 to the CCD camera 11, such that the setup of the CCD camera 11 is performed. Then, the CCD camera 11 captures an image according to the imaging condition of the second group Gr2 (the step S2). Subsequently, in the step S3, in the raw image captured by the CCD camera 11 (image of the entire view field region 20), the image (captured image) of the imaging range of the second group Gr2 is transmitted from the CCD camera 11 to the image processing device main body 12. In the step S4, the image processing device main body 12 receives the captured image and performs the same image process as that in the related art.

After the image of the second group Gr2 is captured and processed, the process returns to the step S1. Here, the imaging range and the imaging condition registered as the third group Gr3 are read from the memory 18, and the signals about the imaging range and the imaging condition of the third group Gr3 are supplied from the image processing device main body 12 to the CCD camera 11, such that the setup of the CCD camera 11 is performed. Then, the CCD camera 11 captures an image according to the imaging condition of the third group Gr3 (the step S2). Subsequently, in the step S3, in the raw image captured by the CCD camera 11 (image of the entire view field region 20), the image (captured image) of the imaging range of the third group Gr3 is transmitted from the CCD camera 11 to the image processing device main body 12. In the step S4, the image processing device main body 12 receives the captured image and performs the same image process as that in the related art.

After the image of the third group Gr3 is captured and processed, the process returns to the step S1. Here, the imaging range and the imaging condition registered as the fourth group Gr4 are read from the memory 18, and the signals about the imaging range and the imaging condition of the fourth group Gr4 are supplied from the image processing device main body 12 to the CCD camera 11, such that the setup of the CCD camera 11 is performed. Then, the CCD camera 11 captures an image according to the imaging condition of the fourth group Gr4 (the step S2). Subsequently, in the step S3, in the raw image captured by the CCD camera 11 (image of the entire view field region 20), the image (captured image) of the imaging range of the fourth group Gr4 is transmitted from the CCD camera 11 to the image processing device main body 12. In the step S4, the image processing device main body 12 receives the captured image and performs the same image process as that in the related art.

If the image of the fourth group Gr4 is captured and processed, in a step S5, it is judged that all groups are processed, and the inspection or measurement of the same inspection object is completed. Then, the image processing device 10 waits until a next inspection object enters the inspection station 17.

Figure 3:
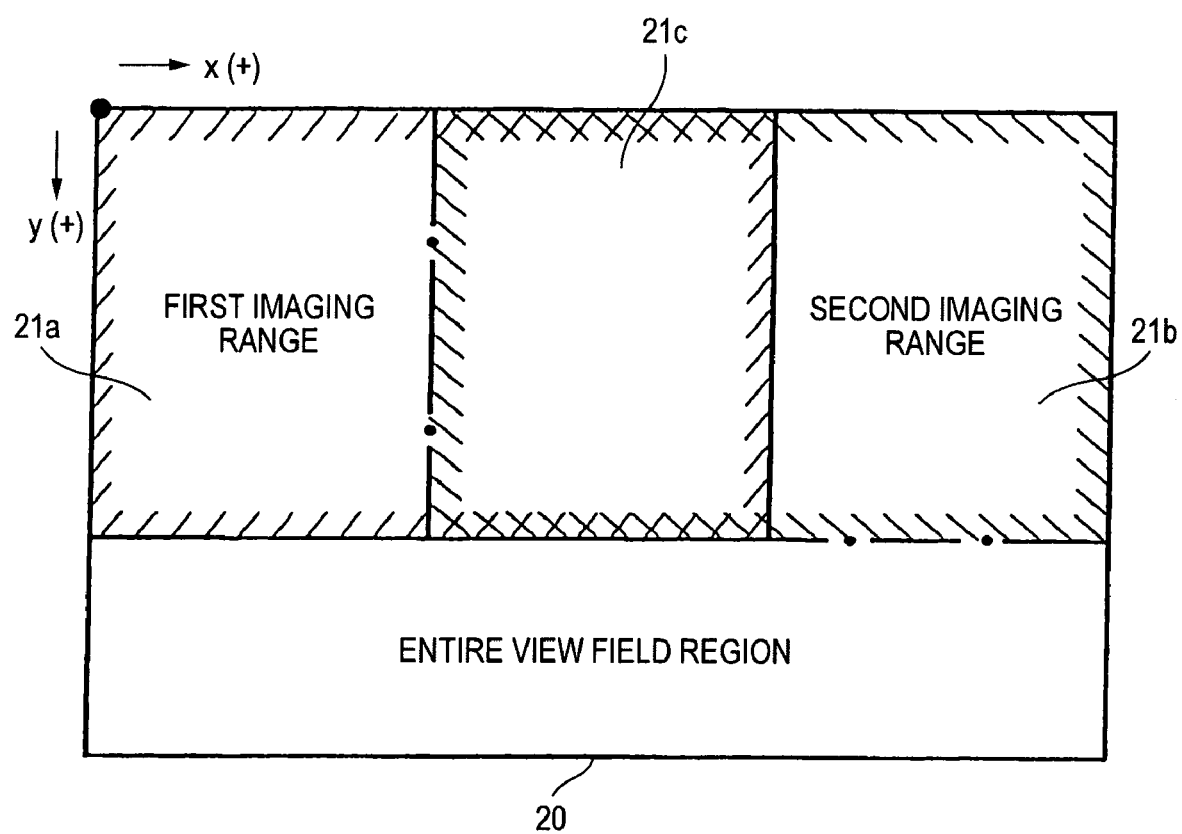
FIG. 3 is a diagram for explaining an imaging region that is set for each group.

For example, as seen from FIG. 3, as regards the image process of an overlap portion 21c of imaging ranges 21a and 21b, when images captured several times are processed as one image, the overlap portion 21c is needed to be processed. In this case, the overlap portion 21c may be averaged to be processed. Further, the captured images may be respectively prioritized and the image process may be performed according to the priority. Alternatively, the captured images may be weighted and the image process may be performed according to the weight.

Further, when plural image processes (for example, from the image process of the first group Gr1 to subsequent image processes) are performed, the imaging range and the imaging condition in the current image process may be selectively changed according to the result of the previous image process. For example, when a tolerance inspection is performed with the image process of the first group Gr1, if the result falls within the tolerance (OK), the setup signals of the imaging range and the imaging condition are transmitted such that an area inspection of an additional location is performed, and the image is captured according to the setup signals of the imaging range and the imaging condition. To the contrary, if the result does not fall within the tolerance (NO), the setup signal for the change of the gain in the imaging range of the first group Gr1 is transmitted to the camera 11, and the image is captured according to the setup signals of the imaging range and the imaging condition, such that the imaging range of the first group Gr1 may be inspected again.

As another example, for example, when a shape matching inspection is performed with the image process of the captured image under the first imaging range and imaging condition, if the shape matches with a first template, the tolerance inspection is subsequently performed with the same imaging range. Further, if the shape matches with a second template, a line defect inspection is subsequently performed with the same imaging range. If the shape does not match with the first or second template, a subsequent inspection may be changed according to the result of the image process such that the subsequent inspection may be not performed.

Another example of a procedure in which the camera 11 captures the image of the inspection object and the image processing device main body 12 receives and processes the captured image will be described with reference to a flowchart of FIG. 6.

Figure 6:
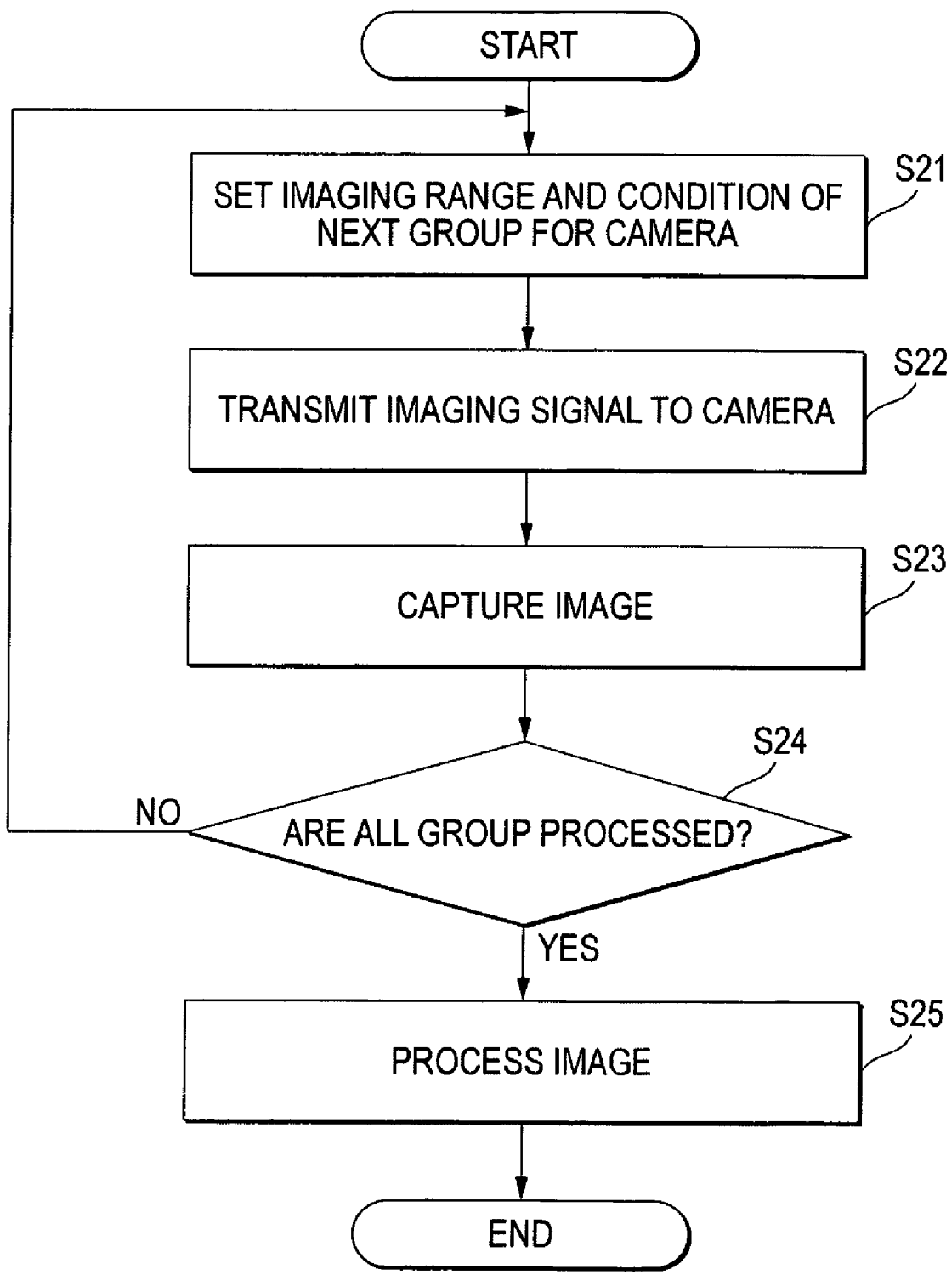
FIG. 6 is a flowchart showing another example of a procedure of a process that is performed by the image processing device according to the present invention.

According to the procedure exemplarily shown in FIG. 6, the image of the imaging range 21 to be transmitted from the CCD camera 11 to the image processing device main body 12 for each group, that is, the captured image is stored in the image processing device main body 12, and, after the images of all groups are captured, the captured images of all groups are processed by the image processing device main body 12.

That is, the inspection object stops at a predetermined position, the image processing device main body 12 synchronously receives the process start signal that is supplied from the exterior, such that the process is started. First, in a step S21, the imaging range and the imaging condition registered as the first group Gr1 are read from the memory 18, and the signals about the imaging range and the imaging condition of the first group Gr1 are supplied from the image processing device main body 12 to the CCD camera 11, such that the setup of the CCD camera 11 is performed. Then, the CCD camera 11 captures an image according to the imaging condition of the first group Gr1 (step S22).

In a next step S23, in the raw image captured by the CCD camera 11 (image of the entire view field 20), the image (captured image) of the imaging range 21a of the first group Gr1 is supplied to the image processing device main body 12. The captured image is received by the image processing device main body 12.

After the image of the first group Gr1 is captured, the process returns to the step S21. Here, the imaging range and the imaging condition registered as the second group Gr2 are set on the CCD camera 11. Then, the CCD camera 11 captures an image according to the imaging range and the imaging condition of the second group Gr2 (the step S22). Subsequently, the image (captured image) of the imaging range 21b of the second group Gr2 is supplied from the CCD camera 11 to the image processing device main body 12 (the step S23).

After the captured image of the second group Gr2 is received by the image processing device main body 12, the process returns to the step S21. Here, the imaging range and the imaging condition registered as the third group Gr3 are set on the CCD camera 11. Then, the CCD camera 11 captures an image according to the imaging condition of the third group Gr3 (the step S22). Subsequently, the image (captured image) of the imaging range 21c of the third group Gr3 is supplied from the CCD camera 11 to the image processing device main body 12 (the step S23).

After the captured image of the third group Gr3 is received by the image processing device main body 12, the process returns to the step S21. Here, the imaging range and the imaging condition registered as the fourth group Gr4 are set on the CCD camera 11. Then, the CCD camera 11 captures an image according to the imaging condition of the fourth group Gr4 (the step S22). Subsequently, the image (captured image) of the imaging range 21d of the fourth group Gr4 is supplied from the CCD camera 11 to the image processing device main body 12 (the step S23).

If the captured image of the fourth group Gr4 is received by the image processing device main body 12, in a step S24, it is judged that all groups are processed, and the process progresses to a step S25. In the step S25, the image processing device main body 12 processes the images of the respective groups. The image process includes the position correction (x, y, θ) of the image about the x axis, the y axis, and the rotation θ, and further it means the process required for the desired inspection or measurement (for example, the size, the existence of defects, the number, the edge detection). The image process including the position correction is well-known, and thus the detailed description thereon will be omitted.

According to the procedure shown in FIG. 6, the captured images of the respective groups are received by and stored in the image processing device main body 12 and the image processing device main body 12 performs the image process after receiving the captured images of all groups. Thus, for the substance (inspection object) transferred to the inspection station at a short tact, the images can be synthesized while preventing blurring from being caused by the movement of the inspection object. In this case, however, the image processing device main body 12 requires the large memory space.

Figure 7:
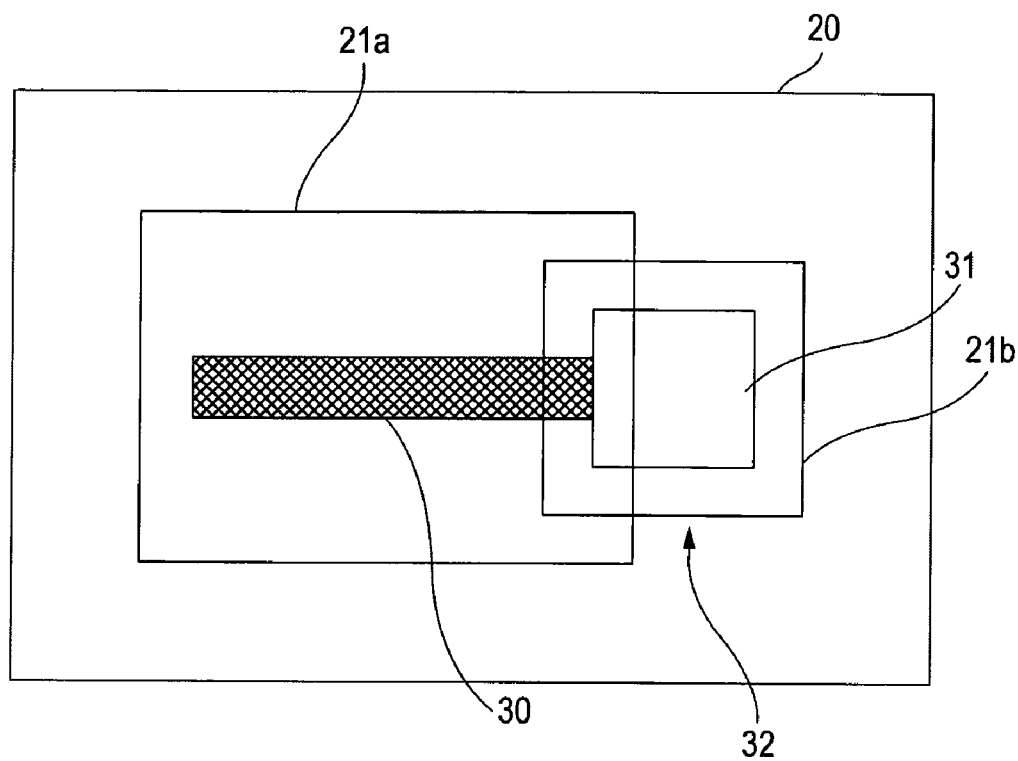
FIG. 7 is a diagram showing an example of an inspection object that can be properly applied to the image processing device according to the present invention.

According to the image processing device 10 of the embodiment, for example, as shown in FIG. 7, for a substance 32 (inspection object) that has regions 30 and 31 having different gray levels, two groups, that is, imaging ranges 21a and 21b for the respective regions 30 and 31 and imaging conditions suitable for the respective regions 30 and 31 are set and registered. Accordingly, proper images for the respective regions 30 and 31 can be received by the image processing device main body 12.

For example, when the first region 30 is made of black resin and the second region 31 is made of a metal, a first portion surrounding the first region 30 is registered as the imaging range of the first group Gr1 and a portion surrounding the second region 31 is registered as the imaging range of the second group Gr2. Further, in the imaging range (the first region 30) registered as the first group Gr1, a relatively slow shutter speed may be registered such that the image does not become dark. Further, in the imaging range (the second region 31) registered as the second group Gr2, a relatively fast shutter speed may be registered such that the image does not have unduly high white levels. To the contrary, when a proper image about the first region 30 is captured, the illumination may become bright, and, when a proper image about the second region 31 is captured, the illumination may become dark, such that the reflection may be prevented. In this case, however, a sufficient response speed cannot be ensured due to the brightness control of the illumination.

Figure 8:
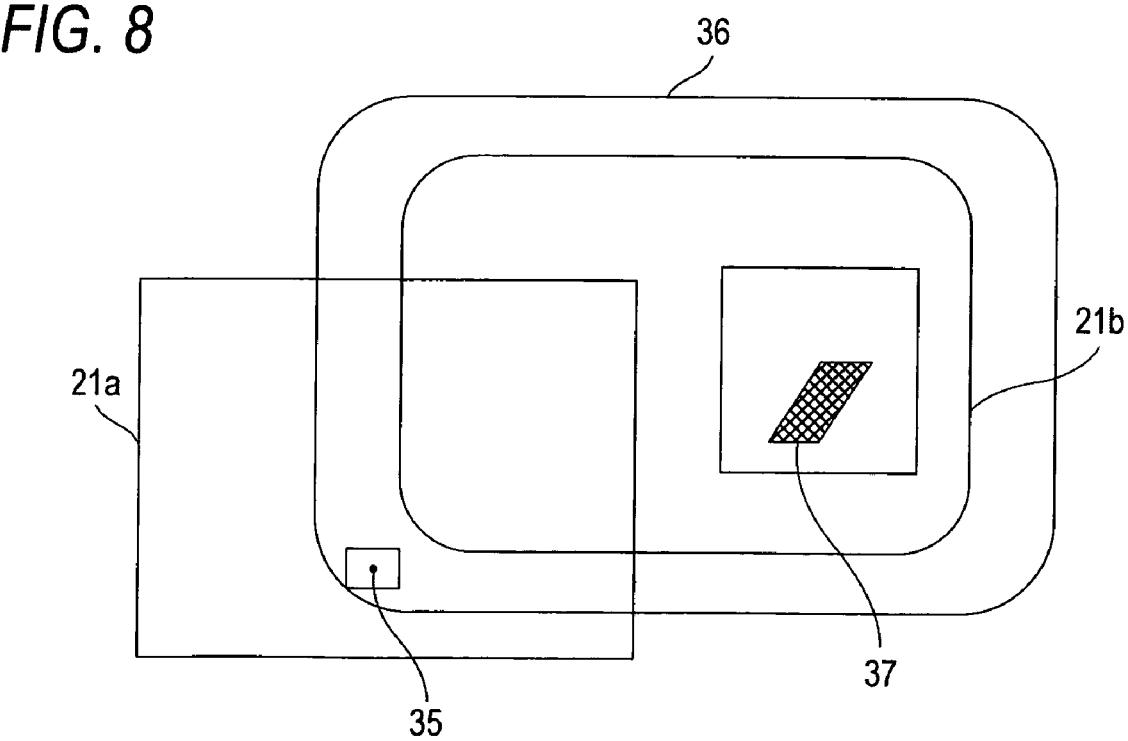
FIG. 8 is a diagram showing another example of an inspection object that can be properly applied to the image processing device according to the present invention.
Figure 9:
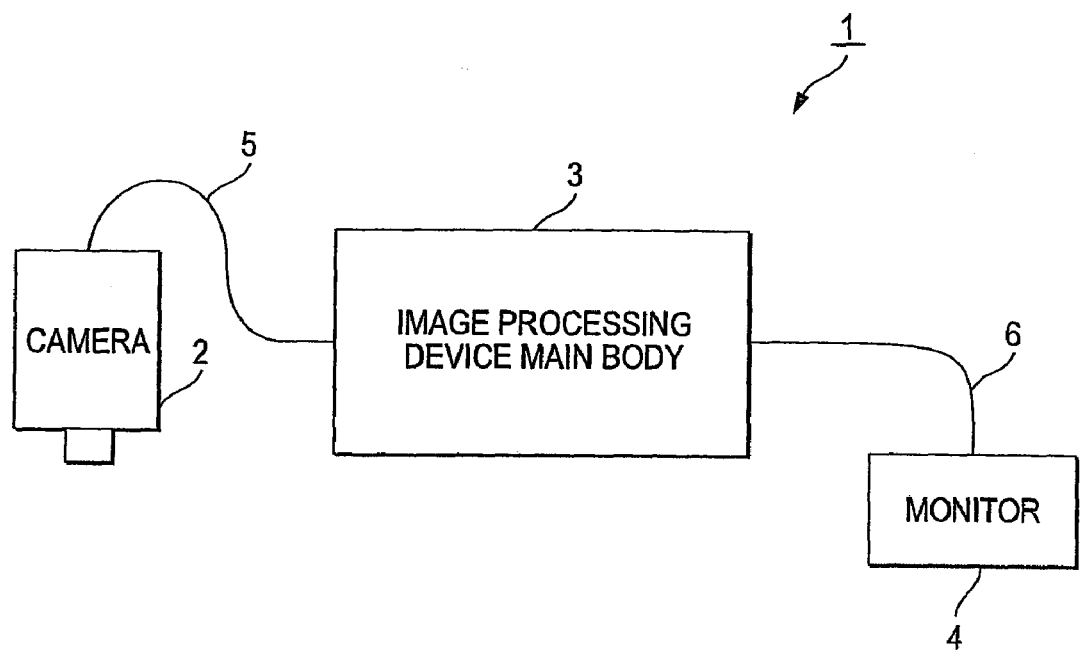
FIG. 9 is a diagram showing an entire configuration of a related-art image processing device.
Figure 10:
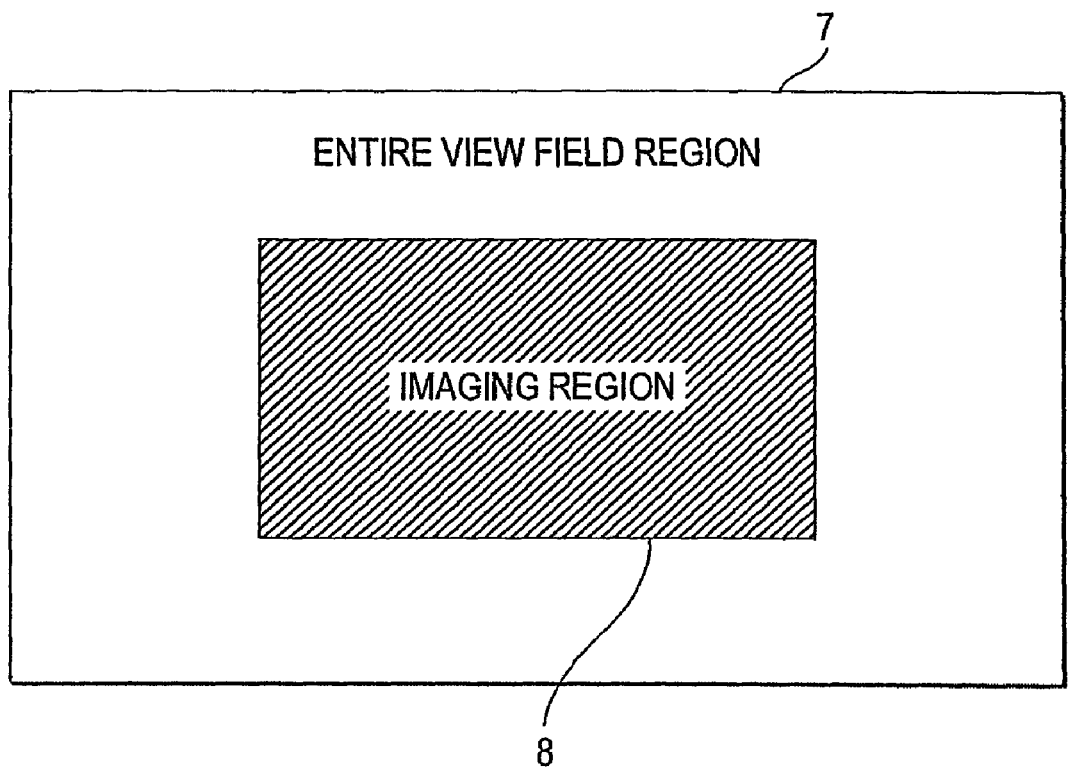
FIG. 10 is a diagram for explaining a related-art image processing method.

Further, as exemplarily shown in FIG. 8, for example, a substance 36 having a positioning mark 35 has the size to an extent that, if not reduced, it cannot be received by the image processing device main body 12. As regards such a substance 36, a portion including the positioning mark 35 that requires inspection precision is registered as a first imaging range 21a, a proper magnification is set for capturing the image of the portion including the mark 35, and the captured image of the first imaging range 21a is received by the image processing device main body 12. Further, a portion including an inspection object 37 in which inspection precision can be ensured with reduced scale is set to a second imaging range 21b and a properly reduced magnification is set for the portion in which inspection precision can be ensured with reduced scale. The captured image of the second imaging range 21b may be received by the image processing device main body 12.

As described above, in the preferred embodiment of the present invention, the image processing device in which the CCD camera 11 and the image processing device main body 12 are connected to each other via the cable 14 is described. Alternatively, the present invention can be properly applied to an image processing device in which the CCD camera 11 and the image processing device main body 12 are incorporated. Similarly, the present invention can be properly applied to an image processing device in which the image processing device main body 12 and the monitor 13 are incorporated. Further, the present invention can be properly applied to an image processing device in which the CCD camera 11, the image processing device 12, and the monitor 13 are incorporated.

Further, the setup of the imaging range and/or imaging condition of the CCD camera 11 may be performed by the signal from the external apparatus. The setup by the signal from the external apparatus may be performed during the image process by the image processing device main body 12.

Further, as a solid-state image element of a camera which can be applied to the present invention, instead of the CCD, a CMOS image sensor may be adapted. In the case of the CMOS image sensor, the advantages according to the present invention can be obtained.

It will be apparent to those skilled in the art that various modifications and variations can be made to the described preferred embodiments of the present invention without departing from the spirit or scope of the invention. Thus, it is intended that the present invention cover all modifications and variations of this invention consistent with the scope of the appended claims and their equivalents.

What is claimed is:

1. An image processing device comprising:
 a solid-state image element camera that captures a plurality of images of an inspection object, the solid-state image element camera comprising a pixel region;
 an image processing device main body that receives and processes the captured images from the camera; and
 a monitor that displays an inspection or measurement result by the image processing device main body,
 the image processing device main body having:
  an assigning section that allows a user to assign a plurality of imaging ranges comprising at least a first imaging range and a second imaging range, and the assigning section allows a user to independently assign a plurality of imaging conditions that includes at least shutter speed for each imaging range and wherein said imaging conditions assigned by user for each imaging range is storable and transmittable, wherein the imaging conditions comprise X and Y coordinates of the pixel region, and the first imaging range and the second imaging range comprise different X and Y coordinates of the pixel region of the solid-state image element camera, wherein the first imaging range and second imaging range are settable so as to be overlapped with each other within the imaging ranges of the solid-state image element camera;
  a storing section having stored therein the plurality of user set imaging ranges of the solid-state image element camera and the plurality of user set imaging conditions including at least one imaging condition for each of the plurality of user set imaging ranges;
  a transmitting section that reads the plurality of user set imaging ranges and the plurality of user set imaging conditions stored in the storing section and transmits a signal about the plurality of user set imaging ranges and the plurality of user set imaging conditions to the solid-state image element camera, in an order for transmitting to the solid-state image element camera which is set in the storing section in addition to correspondence relationship information on the user set imaging condition assigned to each user set imaging range;

a receiving section that receives, as individual image signals, a captured image signal of each of the plurality of user set imaging conditions of the solid-state image element camera, including shutter speed, in a predetermined order, which is set with respect to each of the plurality of user set imaging ranges; and an image processing section that performs a selected inspection or measurement based on each of the captured images obtained in correspondence with each of the imaging ranges, wherein each imaging range is only a portion of the entire field of view of the solid state image element camera and the image processing device performs an image process of at least the first imaging range and the second imaging range based on the captured image signals received by the receiving section and forms a captured image from the plurality of captured image signals;

wherein the solid-state image element camera captures each of the images based on the imaging range and the imaging condition corresponding to the imaging range transmitted in a predetermined order from the transmitting section of the image processing device main body, and transmits each of the captured images to the image processing device.

2. The image processing device according to claim 1, wherein at least one imaging range of the plurality of imaging ranges of the solid-state image element camera is set by an external apparatus connected to the image processing device main body.

3. The image processing device according to claim 2, wherein at least one imaging range of the plurality of imaging ranges of the solid-state image element camera is set by the external apparatus during the image process by the image processing device main body.

4. The image processing device according to claim 1, wherein the image processing device main body reads at least one imaging condition of the plurality of imaging conditions, together with the respective imaging range, and transmits signals about the at least one imaging condition and respective imaging range to the solid-state image element camera, and sets the at least one imaging condition on the solid-state image element camera to capture an image.

5. The image processing device according to claim 4, wherein at least one imaging condition of the plurality of imaging conditions is selected from at least one of a group of magnification and scanning modes of the solid-state image element camera, an amplification factor of an output signal of the solid-state image element camera, diaphragms, and illumination of the solid-state image element camera.

6. The image processing device according to claim 1, wherein the solid-state image element camera and the image processing device main body are connected to each other via a cable.

7. An image processing device having:
a solid-state image element camera that captures a plurality of images of an inspection object, the solid-state image element camera comprising a pixel region;

an image processing device main body that receives and processes a plurality of images, to form a captured image; and a monitor that displays an inspection or measurement result by the image processing device main body, wherein the image processing device main body is switchable between a setup mode in which a user assigns a plurality of imaging ranges and a plurality of imaging conditions such that each imaging range represents only a portion of the entire field of view of the solid-state image element camera, and the plurality of imaging conditions includes at least one imaging condition that includes at least shutter speed for each of the plurality of imaging ranges and wherein said imaging conditions assigned by user for each imaging range is storable and transmittable, wherein the plurality of imaging ranges comprises at least a first imaging range and a second imaging range, the imaging conditions comprise X and Y coordinates of the pixel region, and the first imaging range and the second imaging range comprise different X and Y coordinates of the pixel region of the solid-state image element camera, wherein the first imaging range and second imaging range are settable so as to be overlapped with each other within the imaging ranges of the solid-state image element camera, and an operation mode in which an image process is performed, in a setup mode, the plurality of imaging ranges and the plurality of imaging conditions are transmitted to the solid-state image element camera, and the captured image transmitted from the solid-state image element camera is displayed on the monitor, such that the user assigns the plurality of imaging ranges and the plurality of imaging conditions through an assigning section, and the plurality of imaging ranges and the plurality of imaging conditions are stored in a storing section, wherein an order for transmitting to the solid-state image element camera is set in the storing section in addition to correspondence relationship information on the user set imaging condition assigned to each user set imaging range, in an operation mode, a signal about the plurality of imaging ranges and the plurality of imaging conditions stored in the storing section is transmitted from the image processing device main body to the solid-state image element camera such that the plurality of imaging ranges and the plurality of imaging conditions of the solid-state image element camera is set, and the image processing device main body receives and processes at least the first imaging range and the second imaging range to form a captured image of each of the plurality of imaging ranges of the solid-state image element camera according to the plurality of imaging conditions;

wherein the solid-state image element camera captures, as individual image signals, each of the images based on the imaging range and the imaging condition, including shutter speed, corresponding to the imaging range transmitted in a predetermined order, which is set with respect to each of the plurality of user set imaging ranges, and transmits each of the captured images to the image processing device.

8. The image processing device according to claim 7, wherein, the images captured by the solid-state image element camera under the imaging conditions assigned by the user is displayed on the monitor, such that the user determines the imaging conditions while viewing the monitor.

9. The image processing device according to claim 1, wherein the image processing device main body has:
- the assigning section that assigns the plurality of imaging ranges and the plurality of imaging conditions on behalf of the user;
- the transmitting section that transmits the plurality of imaging ranges and the plurality of imaging conditions assigned by the assigning section to the solid-state image element camera;
- the receiving section that receives the signal about the captured images of the assigned imaging ranges from the solid-state image element camera;
- the image processing section that performs a selected inspection or measurement based on each of the captured images obtained in correspondence with each of the imaging ranges;
- a monitor display control section that transmits the captured images received from the solid-state image element camera to the monitor and causes the monitor to display the captured image; and
- the storing section that stores the plurality of imaging ranges and the plurality of imaging conditions determined by the user.

10. The image processing device according to claim 4, wherein the image processing device main body has:
- the assigning section that assigns at least one imaging range and the at least one imaging condition for that imaging range, on behalf of the user;
- the transmitting section that transmits the at least one imaging range and the at least one imaging condition for that imaging range, assigned by the assigning section, to the solid-state image element camera;
- the receiving section that receives the signal about the captured image of the assigned imaging range captured under the assigned at least one imaging condition, from the solid-state image element camera;
- the image processing section that performs a selected inspection or measurement based on each of the captured images obtained in correspondence with each of the imaging ranges;
- a monitor display control section that transmits the captured image received from the solid-state image element camera to the monitor and causes the monitor to display the captured image; and
- the storing section that stores the at least one imaging range and the at least one imaging condition for that imaging range, determined by the user.

11. An image processing method performed in an image processing device, comprising:
- assigning a plurality of user set imaging ranges and a plurality of user set imaging conditions, pertaining to a solid-state image element camera, through an assigning section of the image processing device, and wherein said imaging conditions assigned by user for each imaging range is storable and transmittable, wherein the plurality of user set imaging ranges comprises at least a first imaging range and a second imaging range, the plurality of user set imaging conditions includes at least one imaging condition that includes shutter speed for each of the plurality of user set imaging ranges, the user set imaging conditions comprise X and Y coordinates of the pixel region, and the first imaging range and the second imaging range comprise different X and Y coordinates of the pixel region of the solid-state image element camera, wherein the first imaging range and second imaging range are set so as to be overlapped with each other within the imaging ranges of the solid-state image element camera;
- storing the plurality of user set imaging ranges of the solid-state image element camera and the plurality of user set imaging conditions including at least one imaging condition for each of the plurality of imaging ranges;
- capturing an image of an inspection object by capturing an image of each of the plurality of imaging ranges of the solid-state image element camera and generating a captured image signal of each image of the plurality of imaging conditions, including shutter speed, captured by the solid-state image element camera, which is set with respect to each of the plurality of user set imaging ranges; and
- performing an image process based on the captured image signal generated;
- wherein each imaging range represents only a portion of the entire field of view of the solid-state image element camera;
- wherein the solid-state image element camera captures each of the images based on the imaging range and the imaging condition corresponding to the imaging range transmitted in a predetermined order from the image processing device, and transmitting each of the captured images to the image processing device.

12. The image processing method according to claim 11, said method further comprising:
- assigning the plurality of imaging ranges and the plurality of imaging conditions set by the user;
- capturing an image of an inspection object by the solid-state image element camera and generating a captured image of the assigned plurality of imaging ranges in the image captured by the solid-state image element camera; and
- displaying the captured image of the assigned plurality of imaging ranges received from the solid-state image element camera; and
- storing the plurality of imaging ranges determined by the user as set imaging ranges of the solid-state image element camera.

13. The image processing method according to claim 11, said method further comprising:
- setting the plurality of imaging ranges of the solid-state image element camera by an external apparatus connected to the image processing device.

14. The image processing device of claim 1, wherein the receiving section of the image processing main body is configured to perform a position correction of the captured image, based upon a previously captured image.

15. The image processing device of claim 7, wherein the image processing device main body is configured to perform a position correction of the captured image, based upon a previously capture image.

16. The image processing method of claim 11, wherein capturing said plurality of images further comprises performing a position correction of the captured image, based upon a previously capture image.

* * * * *